US010933721B2

(12) United States Patent
Pirovolikos et al.

(10) Patent No.: US 10,933,721 B2
(45) Date of Patent: Mar. 2, 2021

(54) AIR FRESHENER HOLDER FOR AUTOMOBILE

(71) Applicants: Steve Pirovolikos, West Hempstead, NY (US); John Fuller, North Arlington, NJ (US)

(72) Inventors: Steve Pirovolikos, West Hempstead, NY (US); John Fuller, North Arlington, NJ (US)

( * ) Notice: Subject to any disclaimer, the term of this patent is extended or adjusted under 35 U.S.C. 154(b) by 0 days.

(21) Appl. No.: 17/063,831

(22) Filed: Oct. 6, 2020

(65) Prior Publication Data

US 2021/0016638 A1    Jan. 21, 2021

Related U.S. Application Data

(60) Provisional application No. 62/929,424, filed on Nov. 1, 2019.

(51) Int. Cl.
  *B60H 3/00*   (2006.01)
  *B60R 11/00*  (2006.01)

(52) U.S. Cl.
  CPC ............ *B60H 3/0014* (2013.01); *B60R 11/00* (2013.01); *B60R 2011/0033* (2013.01)

(58) Field of Classification Search
  CPC .................. B60H 3/0014; B60R 11/00; B30R 2011/0033; A61L 9/12
  USPC ........................................................ 96/222
  See application file for complete search history.

(56) References Cited

U.S. PATENT DOCUMENTS

| | | | | |
|---|---|---|---|---|
| 2,341,048 A | * | 2/1944 | Kopp | B60R 13/10 248/231.41 |
| 2,535,575 A | * | 12/1950 | Hodges, Sr. | B60R 1/12 40/649 |
| 4,598,982 A | * | 7/1986 | Levine | B60R 1/081 359/865 |
| D345,787 S | * | 4/1994 | Martin | D23/366 |
| 5,407,642 A | * | 4/1995 | Lord | A61L 9/12 239/55 |
| 5,478,505 A | * | 12/1995 | McElfresh | B60H 3/0007 261/30 |
| D366,107 S | * | 1/1996 | Shaffer | D20/18 |
| D385,025 S | * | 10/1997 | Ho | D23/366 |
| D476,726 S | * | 7/2003 | Rosenberg | D23/366 |
| D606,185 S | * | 12/2009 | Wefler | D23/366 |
| 2003/0200690 A1 | * | 10/2003 | Galloway | A47G 1/0616 40/779 |

(Continued)

FOREIGN PATENT DOCUMENTS

JP   63001264 A  *  1/1988
JP   3188441 U   *  1/2014

*Primary Examiner* — Hilary L Gutman
(74) *Attorney, Agent, or Firm* — Barry Choobin; Patent 360

(57) ABSTRACT

An air freshener holder for use in automobiles having cabins is dimensioned to removably attach to a rear-side of a rear-view mirror of the automobile. The air freshener holder includes an elongated enclosure having a top, bottom, and side walls defining a volume of the enclosure. A wing-shaped pair of flaps extend from the bottom of the enclosure. The flaps are semi-flexible and can attach to the rear side of a rear-view mirror. The enclosure having an opening for receiving the air-freshener cartridge and a number of apertures for air flow. A transponder can be attached to the top wall of the enclosure.

6 Claims, 5 Drawing Sheets

(56) References Cited

U.S. PATENT DOCUMENTS

| | | | | |
|---|---|---|---|---|
| 2007/0039750 A1* | 2/2007 | Jantelezio | ........... | B60R 11/0264 |
| | | | | 174/50 |
| 2007/0040679 A1* | 2/2007 | Klosinski | ......... | G06K 19/07749 |
| | | | | 340/572.1 |
| 2010/0051664 A1* | 3/2010 | Para | ........................ | B60R 11/02 |
| | | | | 224/545 |
| 2014/0340770 A1* | 11/2014 | Barniak, Jr. | .............. | B60R 1/10 |
| | | | | 359/802 |

\* cited by examiner

AIR FRESHENER HOLDER FOR AUTOMOBILE

CROSS-REFERENCE TO RELATED APPLICATIONS

This application claims priority to the U.S. provisional patent application Ser. No. 62/929,424, filed on Nov. 1, 2019, which is incorporated herein by reference in its entirety.

FIELD OF INVENTION

The present invention generally relates to an air freshener holder, and particularly the present invention relates to an air freshener holder that can be attached to a rear-view mirror of the automobile.

BACKGROUND

Air fresheners are popularly used in closed environments to make the air smell fresh. Air fresheners generally include substances that mask or remove unpleasant odors from the air. Additionally, the air fresheners include fragrances that mask the unpleasant odor and make the air smell pleasant. Air fresheners are also used in automobiles having closed environments for making the air feel pleasant. The automobiles with a closed environment include cars, trucks, utility vehicles that have cabins.

In automobiles, air fresheners are commonly used in a variety of forms including liquid, gels, and solid forms. The fragrance substances are slowly and continuously diffused into the environment for keeping the air pleasant. The positioning of the air freshener in automobiles is important for the uniform distribution of the fragrance substances in the cabin of the automobile. The location should have a good airflow that allows the diffused fragrance substances to be carried and diffuse in the air of the cabin. Many commercial air freshener products are designed to be hung from the rearview mirror. Although, the location near the windshield is having a good airflow, however, the air freshener product hung from the rear-view mirror can obstruct the view of the driver and may also lead to an accident. Many countries, including the United States of America, have strict laws against putting any article near a windshield that can obstruct the view of the driver.

Thus, a need is appreciated for a multipurpose air freshener holder that is easy to install and does not hinder the view of the driver.

The term "automobile" hereinafter connotes to an automobile that has a cabin, wherein the cabin is provided with at least one door and optionally windows.

SUMMARY OF THE INVENTION

The principal object of the present invention is therefore directed to a compact and easy to install air freshener holder for automobiles.

It is a further object of the present invention that the air freshener holder does not hinder the view of the driver.

It is an additional object of the present invention that the air freshener holder is a multi-utility article.

It is another object of the present invention that the air freshener holder is easy to install.

It is a further object of the present invention that the air freshener holder is economical to manufacture.

In one aspect, disclosed is an air freshener holder for use in automobiles having cabins. The air freshener holder disclosed herein is dimensioned to removably attached to the rear side of a rear-view mirror of an automobile. The air freshener holder includes an elongated enclosure having a top, bottom, and side walls defining the volume of the enclosure. A wing-shaped pair of flaps are configured on the bottom of the enclosure. The flaps are rigid, but flexible enough to conform to the variable shapes the rear-view mirrors. The enclosure further having a plurality of apertures for the airflow.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
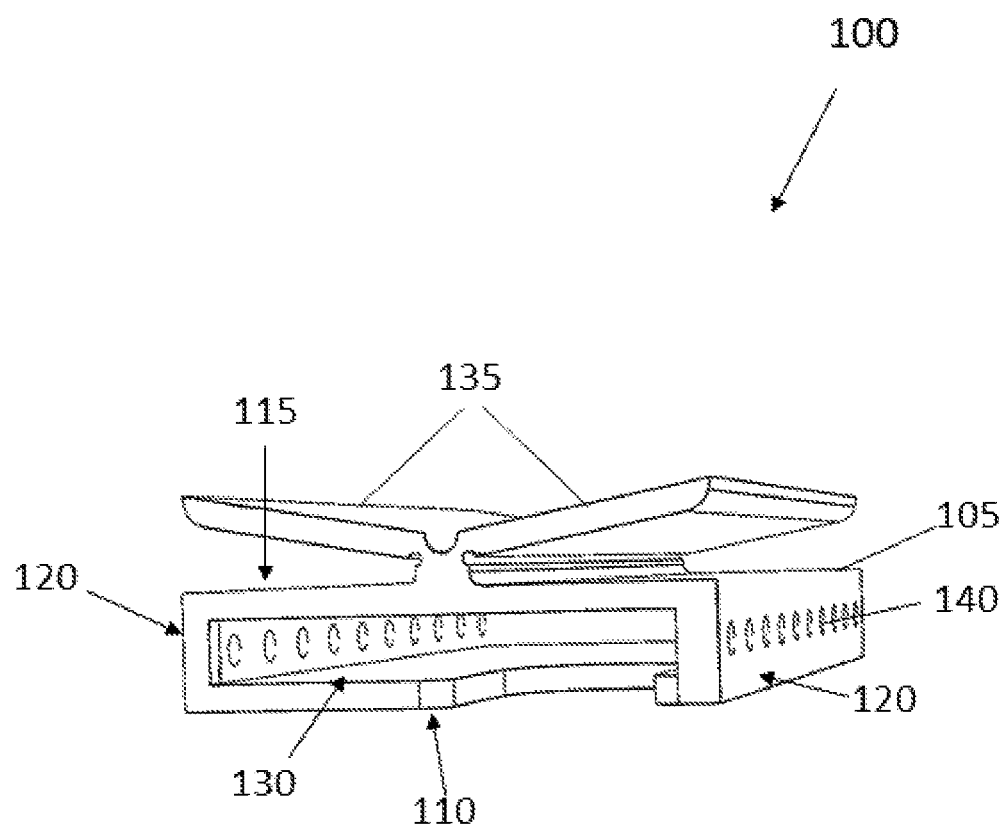
FIG. 1 is a perspective view of the air freshener holder, according to an exemplary embodiment of the present invention.

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as devices and methods of use thereof. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

The following detailed description is described with reference to the drawings, wherein like reference numerals are used to refer to like elements throughout. In the following description, for purposes of explanation, specific details may be set forth in order to provide a thorough understanding of the subject innovation. It may be evident, however, that the claimed subject matter may be practiced without these specific details.

Disclosed is an air freshener holder for use in automobiles for holding suitable air freshener cartridges. The air freshener holder can removably attach to the rear-side of a rear-view mirror of an automobile. Herein, the automobile can be any automobile having a closed environment, such as cabins. The air freshener holder includes an enclosure similar to a ventilated housing or a casing. The enclosure having an opening to receive the air freshener cartridge. The enclosure can retain the cartridge, for example, by including a locking mechanism that engages with the cartridge. Alternatively, the cartridge can snugly fit into the enclosure. Still, alternatively, the enclosure can be capped. The cap can be of a meshed configuration that allows ventilation of the interior of the enclosure. A suitable number of apertures can be configured in the enclosure for enhancing ventilation. Proper ventilation allows the fragrance material from the cartridge to uniformly diffuse into the inner environment of the automobile's cabin.

The air freshener holder further comprises a pair of flap configured as a wing that is rigid, but flexible enough to conform to the shape of the rear side of rear-view mirrors. Rear-view mirrors are commercially available in a range of sizes and shapes. In particular, the rear-side of the housing of the rear-view mirrors can be flat or curved. The wing-shaped flaps of the disclosed air freshener holder can conform to different shapes of the rear side of the rear-view mirror. The air freshener holder can be attached to the rear-view mirror using an adhesive, such as double-sided tape.

In one implementation, the top of the enclosure of the air freshener holder faces the windshield and will be visible from the outside of the automobile. Images and notes for conveying information can be attached to the top of the air freshener holder. For example, images, advertising materials, parking passes, federal ID tags, and logos. The image, notes, or logo as a sticker can be applied to the air freshener holder.

Besides the images and notes, to the top of the enclosure can also be attached toll-road transponders. The toll-road transponder attached to the air freshener holder can be easily visible from the outside of the automobile and can also be easily accessed or scanned. The toll-road transponders can be attached using a fastener, such as an adhesive, magnets, hook and look fasteners, and like. Double-sided tapes can be used to attach a device quickly and conveniently, such as the transponder can be attached to the air freshener holder using the double-sided tape.

Figure 2:
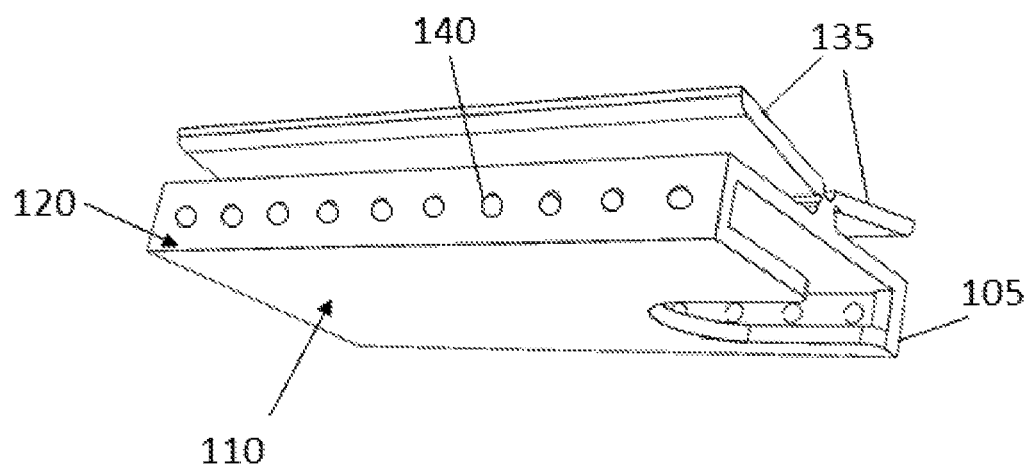
FIG. 2 is a side perspective view of the air freshener holder of FIG. 1.
Figure 3:
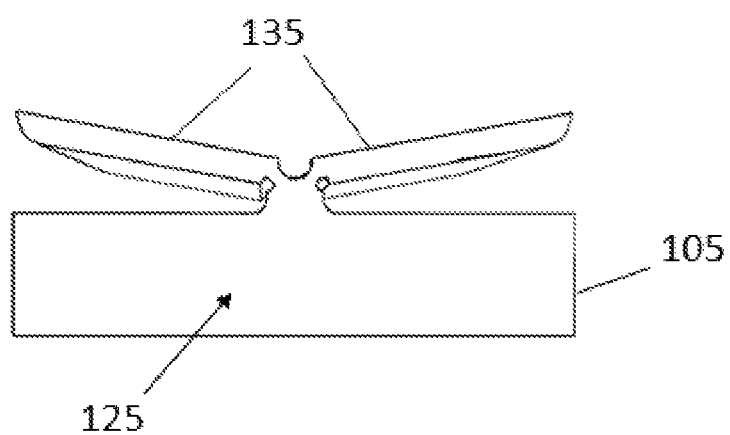
FIG. 3 is a rear view of the air freshener holder of FIG. 1.

Now referring to FIG. 1-3, which shows one implementation of the air freshener holder 100. The air freshener holder 100 includes an enclosure 105 that is having a top 110, a bottom 115, opposite left and right sides 120, and a rear side 125 (shown in FIG. 3). The front side 130 of the enclosure 105 is open and can receive an air freshener cartridge, also referred hereinafter as "cartridge". A curved shaped cut can be seen in the front wall along with the opening. Through the cut, a portion of the cartridge is accessible to slide out the cartridge from the enclosure. The enclosure shown in the FIG. 1-3 is of a cuboidal shape, however, it is to be understood that the enclosure of the air freshener holder can be made in assorted shapes and sizes. For example, different shapes like cube, polygon, and round are within the scope of the present invention.

Further can be seen in FIG. 1 is a pair of flaps 135 that extends from the bottom 115 of the enclosure 105 and directs in opposite directions. Each flap is at an acute angle relative to the bottom of the enclosure resembling a wing-like configuration. The wing-shaped flaps 135 are rigid, but flexible enough to conform to the distinct shapes of the rear-side of the rear-view mirrors. In one case, the winged flaps can be made of a combination of polypropylene, polyethylene mixed with thermal elastic to provide the desired flexibility. The enclosure can be made of the same material as that the winged flaps. Alternatively, the enclosure can be made of any suitable material that is durable and rigid including plastics, metals, alloys, and like.

The enclosure can be provided with several apertures 140 for the airflow. In FIGS. 1 and 2, the apertures can be seen on opposite sides of the enclosure. The number and positioning of the apertures can be varied. Through the apertures, the air carrying the fragrance substances can pass, wherein the opening of the enclosure and the apertures provide airflow for carrying the fragrance substances into the cabin of the automobile.

Figure 4:
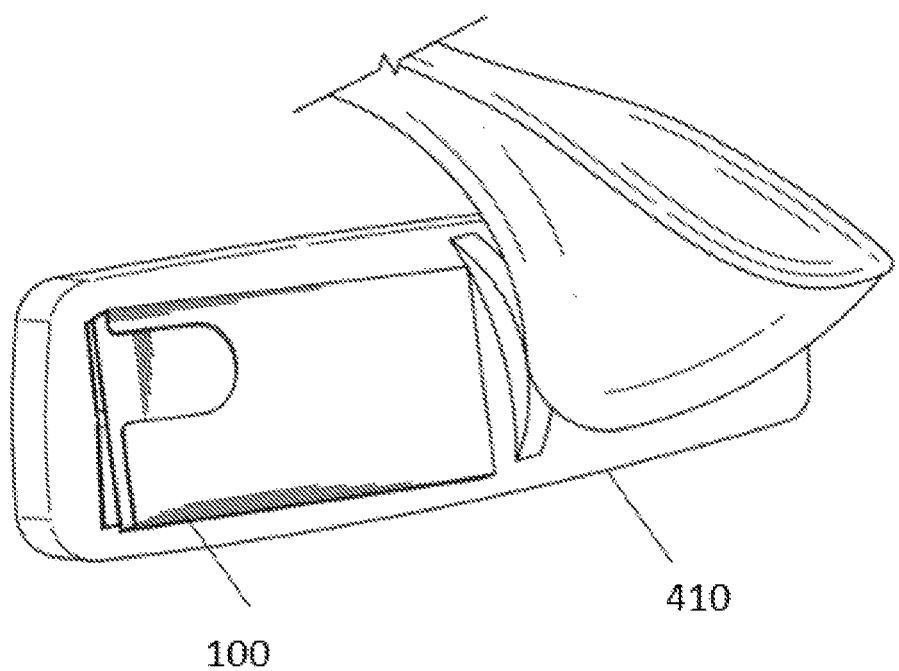
FIG. 4 shows the air freshener holder attached to a rear-view mirror, according to an exemplary embodiment of the present invention.
Figure 5:
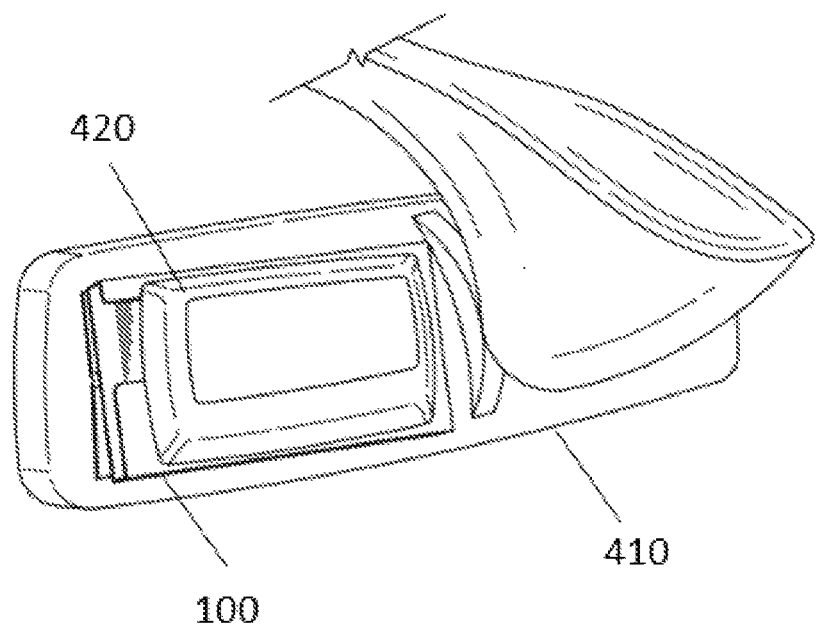
FIG. 5 shows a transponder attached to the air freshener holder of FIG. 4.

FIG. 4 shows the air freshener holder 100 attached to the rear-view mirror 410. Shown in FIG. 4 are the winged flaps of the air freshener holder attached to the rear-side of the rear-view mirror. FIG. 5 shows a transponder 420 attached to the top of the enclosure of the air freshener holder 100.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. An air freshener holder for an automobile, the air freshener holder comprising:
    an enclosure having a top wall, a bottom wall, a left wall, a right wall, and a rear wall defining a volume of the enclosure, the enclosure having an opening on the front for receiving an air freshener cartridge, a plurality of apertures in the left wall and the right wall of the enclosure;
    a semi-flexible wing-shaped pair of flaps extend, at an acute angle, from the bottom wall of the enclosure, the pair of flaps configured to attach using an adhesive to a rear face of a rear-view mirror.

2. The air freshener holder of claim 1, wherein the top wall of the enclosure is flat.

3. The air freshener holder of claim 1, wherein the enclosure is cuboid.

4. The air freshener holder of claim 1, wherein the top wall of the enclosure is having a curved cut along the front opening.

5. The air freshener holder of claim 1, wherein the air freshener holder further comprises an air freshener cartridge interchangeably received into the enclosure.

6. The air freshener holder of claim 5, wherein the air freshener holder further comprises a transponder attached to the top wall of the enclosure.

\* \* \* \* \*